United States Patent

Ambrus et al.

[11] Patent Number: 6,071,412
[45] Date of Patent: Jun. 6, 2000

[54] EXTRACORPOREAL DEVICE CONTAINING IMMOBILIZED CHELATOR ON SILICA SUBSTRATE AND USE THEREOF

[75] Inventors: Clara M. Ambrus, Buffalo; Agnes Stadler, West Amherst, both of N.Y.

[73] Assignee: Hemex, Inc., Buffalo, N.Y.

[21] Appl. No.: 09/123,029

[22] Filed: Jul. 27, 1998

[51] Int. Cl.[7] .......................... B01D 61/00; B01D 63/02; B01D 63/06
[52] U.S. Cl. ................. 210/638; 210/321.79; 210/321.8; 210/321.88; 210/321.89; 210/500.23; 210/651
[58] Field of Search .......................... 210/321.79, 321.8, 210/321.88, 321.89, 198.2, 500.23, 638, 651; 436/524, 528; 502/407; 435/2

[56] References Cited

U.S. PATENT DOCUMENTS

| | | | |
|---|---|---|---|
| 4,612,122 | 9/1986 | Ambrus et al. | 210/638 |
| 4,714,556 | 12/1987 | Ambrus et al. | 210/638 |
| 4,787,974 | 11/1988 | Ambrus et al. | 210/321.8 |

OTHER PUBLICATIONS

Ambrus et al., , ASAIO, 10(3):749–752 (1987).
Anthone et al., ASAIO, 10(3):744–748(1987).
Anthone et al., J Am Soc Nephrol 6:1271–1277 (1995).
Fadeeva et al., Analytica Chimica Acta 219:201–212 (1989).
Glennon and Srijaranai, Analyst 115:627–630 (1990).
Giesche and Matijevic, Dyes and Pigments 17:323–340 (1991).

*Primary Examiner*—John Kim
*Attorney, Agent, or Firm*—Braman & Rogalskyj, LLP

[57] ABSTRACT

In an improved process for immobilizing a chelator moiety on a silica substrate, the substrate is reacted in a liquid reaction medium with an alkyltrialkoxysilane compound having a functional group that provides an attachment site for covalently binding the chelator moiety to the substrate. The improvement comprises providing a particulate silica substrate having a surface area of less than about 50 $m^2/g$. An improved extracorporeal device for removing metal ions from blood and other fluids includes a cartridge having an inlet and an outlet and containing a plurality of tubular fibers that extend from the inlet to the outlet. Each fiber has a lumen enclosed by an anisotropic membrane. The membrane is supported by a macroporous structure that contains a chelator moiety immobilized on a particulate silica substrate having a surface area of less than about 50 $m^2/g$. The anisotropic membrane forms a diffusion barrier that is permeable to metal cations contained in the fluid but is substantially impermeable to high molecular weight components. A method of removing chelatable metal cations from blood fluid uses the described extracorporeal device. The blood fluid containing the chelatable cations is passed through the lumen of each tubular fiber and diffused through the anisotropic membrane enclosing each lumen. The cations are contacted with the immobilized chelator moieties in the macroporous structure supporting the membrane, which causes the cations to be immobilized in the macroporous structure. The metal cations are thereby effectively removed from the fluid.

11 Claims, 1 Drawing Sheet

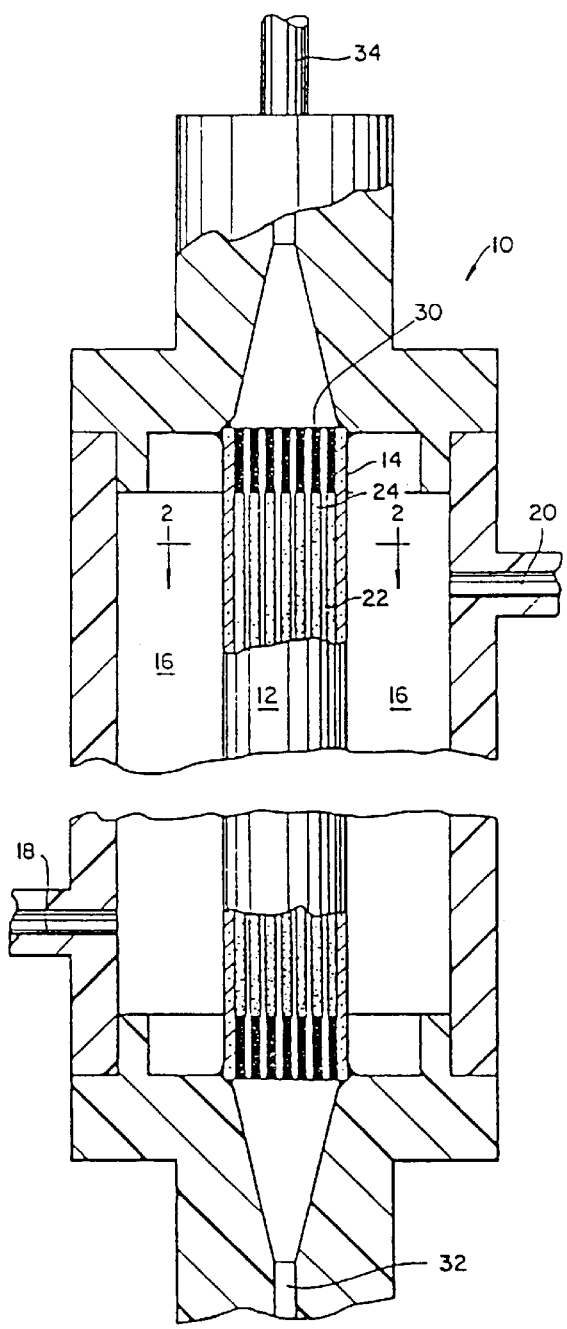
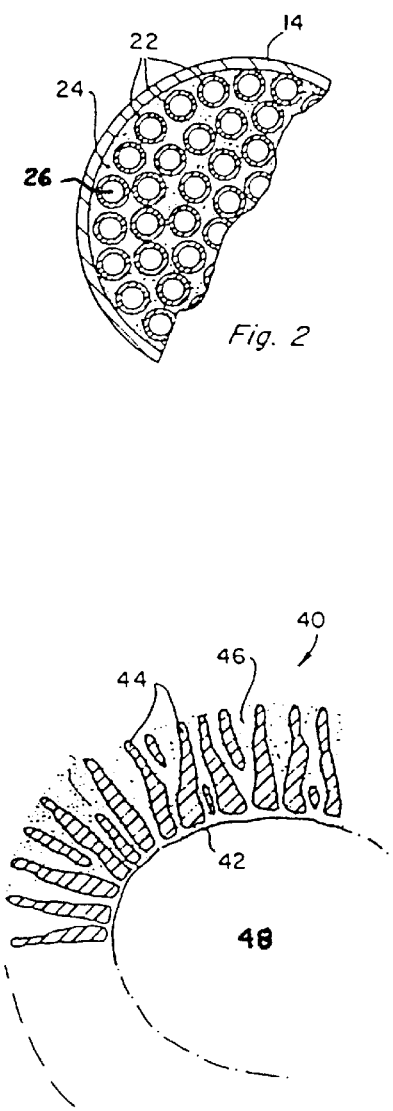
Fig. 2
Fig. 3
Fig. 1

EXTRACORPOREAL DEVICE CONTAINING IMMOBILIZED CHELATOR ON SILICA SUBSTRATE AND USE THEREOF

FIELD OF THE INVENTION

The subject invention is directed generally to chelators and, more particularly, to a process for immobilizing a chelator on silica, an extracorporeal device comprising the immobilized chelator, and a method of removing a particular chelatable agent from blood and other fluids using the extracorporeal device.

BACKGROUND OF THE INVENTION

Patients with End Stage Renal Disease (ESRD) managed with chronic hemodialysis often have severe aluminum toxicity. This may be caused by the aluminum-containing medication given to these patients to keep blood phosphate levels in balance, by aluminum in the dialysate fluid, by diet, or by increased aluminum absorption from the intestines.

Depending of the level of aluminum in the blood, its toxicity may have different manifestations. Aluminum levels above 60 $\mu$g/L may cause anemia unresponsive to treatment with erythropoietin, and osteodystrophy with severe enough bone pain to keep patients wheelchair bound. A level of 100 $\mu$g/L or more will result in progressive brain damage leading to death in 12 months or less. In the U.S. alone, hundreds of thousands of patients with ESRD are treated with chronic hemodialysis.

A second population at potential risk for aluminum toxicity includes individuals with dental and heart valve implants, and orthopedic replacement joints. These prostheses often have parts containing aluminum alloys to increase weight bearing or to decrease calcification. Aluminum leaching from such implants may cause toxicity over time, particularly in diabetic or elderly individuals with compromised kidney function.

Patients with aluminum intoxication are currently treated with intravenous infusions of desferrioxamine (DFO) given 1–3 times weekly. The complex formed between the DFO and the aluminum circulating in the blood is expected to be removed by dialysis. Reduction of aluminum to "sub-toxic levels" (under 30 $\mu$g/L) may take 8 to 12 months, during which time the patient is exposed to the toxicity of aluminum as well as the toxicity of DFO. For that reason, today this treatment is restricted to patients with high aluminum levels (100 $\mu$g/L or more) . Acute side-effects of DFO infusion include hypotension and acute loss of visual acuity which is, however, reversible. Increased incidence of systemic bacterial infections as well as lethal fungal infections may also accompany treatment of patients with DFO.

Medical devices comprising cartridges containing inactivated charcoal have been introduced for the removal of aluminum from a patient's blood. However the devices cause damage to the blood cells as they flow through the charcoal in the cartridges.

In addition to aluminum, other metals present in contaminated environments can accumulate in a person's body and cause substantial health problems. Such metals include, for example, iron, lead, copper, cadmium, mercury, nickel, zinc, and plutonium. The cations of all of these metals undergo reaction with typical multivalent chelating agents to form metal chelate complexes that can be separated and removed from the reaction site.

U.S. Pat. No. 4,612,122 to Ambrus and Horvath, the disclosure of which is incorporated herein by reference, describes an extracorporeal device for removing metal cations from blood using an immobilized chelating agent. As blood flows through the device, the cations react with the chelating agent to form a complex that is retained in the device, resulting in detoxification of the blood.

A device similar to that described in U.S. Pat. No. 4,612,122 and containing the chelating agent desferrioxamine (DFS) has been employed to remove aluminum and iron from blood, as described in Anthone et al., "Immobilized Desferrioxamine (DFO) for the Extracorporeal Removal of Aluminum" in *ASAIO*, 1987, Vol. 10, No. 3, pages 744–748; Anthone et al., "Treatment of Aluminum Overload Using a Cartridge With Immobilized Desferrioxamine" in *J. Am. Soc. Nephrol.*, 1995, Vol. 5, pages 1271–1277; and Ambrus et al., "Extracorporeal Removal of Iron with Immobilized Desferrioxamine" in *ASAIO*, 1987, Vol. 10, No. 3, pages 749–752, the disclosures of which are incorporated herein by reference.

Immobilized chelating agents are useful for removing metal cations from substances other than blood. For example, Glennon et al., "Biochelator Cartridge for the Solid-Phase Extraction of Trace Metals" in *Analyst*, 1990, Vol. 115, pages 627–630, the disclosure of which is incorporated herein by reference, describes hydroxamic acid chelating agents, including desferrioxamine (DFO), immobilized in silica and used for separation of various metal cations from sea water. Also, Fadeeva et. al., "Preparation, Properties and Analytical Application of Silica with Chemically Grafted Hydroxamic Acid Groups" in *Analytica Chimica Acta*, 1989, Vol. 219, pages 201–212, the disclosure of which is incorporated herein by reference, describes the attachment of propanohydroxamic acid groups to silica having a surface area of 80 m$^2$/g. The resulting sorbents are used to remove trace amounts of metals such as molybdenum (VI), zirconium (IV), and vanadium (V).

The efficiency of metal cation removal using the device described in U.S. Pat. No. 4,612,122 and the above-cited references depends considerably on the amount of a chelating agent such as DFO that is immobilized within the device. Accordingly, a process that can provide for the immobilization of larger amounts of DFO per amount of silica substrate, while allowing the device to function effectively to remove aluminum and other cations, would be highly desirable. This result is achieved by the present invention.

SUMMARY OF THE INVENTION

The present invention is directed to an improved process for immobilizing a chelator moiety on a silica substrate. The substrate is reacted in a liquid reaction medium with an alkyltrialkoxysilane compound having a functional group that provides an attachment site for covalently binding the chelator moiety to the substrate. The improvement comprises providing a particulate silica substrate having a surface area of less than about 50 m$^2$/g.

Also in accordance with the present invention is an improved extracorporeal device for removing metal ions from blood and other fluids. The device includes a cartridge having an inlet and an outlet and containing a plurality of tubular fibers that extend from the inlet to the outlet. Each fiber has a lumen enclosed by an anisotropic membrane. The membrane is supported by a macroporous structure that contains a chelator moiety immobilized on a particulate silica substrate having a surface area of less than about 50 m$^2$/g. The anisotropic membrane forms a diffusion barrier that is permeable to metal cations contained in the fluid but is substantially impermeable to high molecular weight components.

Further in accordance with the present invention is a method of removing chelatable metal cations from blood and other fluids using the just described extracorporeal device. The fluid containing the chelatable cations is passed through the lumen of each tubular fiber and diffused through the anisotropic membrane enclosing each lumen. The cations are contacted with the immobilized chelator moieties in the macroporous structure supporting the membrane, which causes the cations to be immobilized in the macroporous structure. The metal cations are thereby effectively removed from the fluid.

BRIEF DESCRIPTION OF THE DRAWINGS

FIG. 1 is a partial schematic cross-sectional view of an apparatus useful in the practice of the invention.

FIG. 2 is a section of FIG. 1.

FIG. 3 is a greatly enlarged cross-sectional view of the fiber membrane structure useful in the practice of the invention.

DETAILED DESCRIPTION OF THE INVENTION

The invention provides a process for immobilizing a chelator moiety on a silica substrate having a surface area of less than about 50 $m^2/g$, preferably less than about 25 $m^2/g$, more preferably less than about 10 $m^2/g$.

As used herein, a chelator refers to a compound, generally an organic ligand molecule capable of forming a ring structure, referred to as a chelate, by the reaction of a metal cation with one or more groups on the organic ligand molecule. Chelation refers to the binding of a metal ion by two or more atoms, typically oxygen or nitrogen, included in the ligand molecule.

Chelators of such metal ions are well known in the art, and include, for example, hydroxamic compounds such as desferrioxamine (DFO) (deferoxamine) and derivatives thereof (desferrioxamine mesylate, Desferal, Deferoxamine methanesulphonate), ethylenediamine, acetylsalicylic acid, dimethylglyoxime (DMG), rhodotorulic acid, diethylenetriamine, triethylenetetramine, and ethylenediaminetetraacetic acid (EDTA). Such chelators having two points of attachment to a central atom are referred to as bidentate chelators, having three points of attachment are referred to as tridentate chelators, having four points of attachment are referred to as tetradentate chelators, etc.

In accordance with the present invention, a chelator moiety is immobilized on a particulate silica substrate. "Immobilized" refers to formation of a covalent linkage between the chelator moiety and the substrate.

The process of the invention provides attachment sites on the silica substrate. These sites are characterized by reactive groups, which may be, for example, primary amino groups or primary carboxy groups. The reactive groups are selected on the basis of their ability to bind to a chelator moiety directly, or to a chelator moiety via a connector moiety. Suitable connector moieties are provided by various difunctional organic compounds such as dialdehydes, for example, glutaraldehyde and succinaldehyde; carboxylic diacid dichlorides, for example, glutaryl dichloride and succinyl dichloride; and carboxylic diacid anhydrides, for example, glutaric anhydride and succinic anhydride. In one preferred embodiment, the reactive groups at the attachment sites are primary amino groups, the chelator moieties are included in desferrioxamine, and the connecting moieties are included in glutaraldehyde.

In the chelator moiety immobilization process of the present invention, which is preferably carried out in the aqueous medium, the functional group included in the alkyltrialkoxysilane reactant can be primary amino, mercapto, epoxy, vinyl, carboxy, carbomethoxy or chlorocarbonyl.

As previously mentioned, a connector moiety can be covalently bound to the functional group at an attachment site on the substrate. The chelator moiety can then be bound to the attached connector moiety, which in one embodiment is included within a dialdehyde compound. In a preferred embodiment of the process of the invention, a primary amino functional group is included in the alkyltrialkoxysilane compound, gammaaminopropyltriethoxysilane, for example, that is reacted in the aqueous medium with particulate silica that has a surface area of about 5 $m^2/g$. The silica can be diatomaceous earth. A preferred chelator moiety is included within desferrioxamine (DFO), and a preferred connector moiety is included within glutaraldehyde. The imino function resulting from the reaction of DFO with glutaraldehyde can be reduced to provide a more stable linkage between the chelator and connector moieties.

The invention also provides an extracorporeal device comprising a cartridge having an inlet and an outlet and containing a chelator moiety immobilized on a silica substrate as described above. The cartridge includes a plurality of tubular fibers extending from the inlet to the outlet. Each hollow fiber comprises a lumen enclosed by an anisotropic membrane. The membranes are supported by a surrounding macroporous structure in which the immobilized chelator moiety is positioned.

As depicted in FIG. 1, a cartridge 10 has an interior processing chamber 12 with an interior glass wall 14. Around chamber 12 is an exterior chamber 16 that is utilized to control the temperature in chamber 12, the temperature of which is kept constant. A temperature-controlling fluid is passed into chamber 16 through lower conduit 18 and passes out of the chamber through upper conduit 20. Chamber 12 contains about five hundred tubular, anisotropic, ultrafiltration membranes 22 of the type generally called "hollow-fiber membranes". These membranes are about 0.3 millimeters in inside diameter and 0.5 millimeters in outside diameter. They have interior retentive membrane walls of about 1 micrometer in thickness and a nominal central conduit path of about 8 inches (20 centimeters).

The membranes are sealed together in matrices of resin 30 at the inlet port 32 and outlet port 34. The resin effectively seals any cross-sectional area that may be left between the membranes and ensures that all fluid entering the apparatus through inlet 32 flows into the tubular membranes 22. As shown in FIG. 2, each of the membranes encloses a lumen 26. Surrounding and supporting membranes 22 is macroporous structure 24, in which is disposed a silica substrate bearing an immobilized chelator prepared by the process of the present invention.

As depicted in FIG. 3, a hollow fiber membrane structure 40 is composed of a single polymeric material that is formed into a tubular section comprising a relatively tight, very thin ultrafiltration membrane 42, which encloses a lumen 48. Each membrane 42 is supported by a relatively porous, exterior structure 44, in which is disposed material 46, a silica substrate on which a chelator moiety has been immobilized by the process of the present invention.

Further provided is a method of removing chelatable metal cations from blood and other fluids using the above-described extracorporeal device. A fluid containing the chelatable ions is passed from the device inlet to its outlet through the lumen of each tubular fiber and diffuses through the anisotropic membrane enclosing each lumen. The metal cations contact the immobilized chelator positioned in the macroporous structure surrounding and supporting the membranes. The chelated ions are immobilized in the macroporous structure, resulting in substantially complete removal of the ions from the fluid.

In a preferred embodiment, the silica substrate contained in the cartridge is diatomaceous earth, and the immobilized chelator moieties are included in desferrioxamine molecules.

The chelatable metal cations removed from a fluid by the method of the present invention include aluminum, iron, lead, copper and mixtures thereof. The method is particularly useful for the removal of aluminum from blood.

U.S. Pat. Nos. 4,714,556 and 4,787,974, to Ambrus and Horvath, the disclosures of which are incorporated herein by reference, describe the selective removal of pathenogenic factors, i.e., antigens, from blood using an extracorporeal apparatus similar to that disclosed in the previously mentioned U.S. Pat. No. 4,612,122. Described in both U.S. Pat. Nos. 4,714,556, and 4,787,974 is the attachment of bovine insulin to a colloidal silica substrate having a high surface area. The initial step for binding insulin to the substrate entails modification of its surface by reaction under non-aqueous conditions in toluene with gamma-aminopropyltrimethoxysilane. This procedure provides reactive sites on the silica substrate for subsequent attachment, via a glutaraldehyde connector moiety, of the insulin.

Giesche and Matijevic, "Well-Defined Pigments: I. Monodispersed Silica-Acid Dyes System"in *Dyes and Pigments,* 1991, Vol.17, pages 323–340, the disclosure of which is incorporated herein by reference, describes the attachment of dyes to spherical silica particles whose surfaces were modified by reaction with gamma-aminopropyltriethoxysilane. Using microcalorimetric measurements, Giesche and Matijevic determined that reaction at elevated temperatures (80° C.) resulted in the attachment of maximum of 87 micromols/g of aminopropyltriethoxysilane molecules to the surface of silica particles having a surface area of 53 $m^2/g$. This corresponds to an area of 58 square angstroms for each aminopropyltriethoxysilane molecule.

By applying these results to Celite Analytical Filter Aid, which has a surface area of about 5 $m^2/g$, it can be calculated that this material could hold a maximum of about 8.7 micromols/g of attached gamma-aminopropyltriethoxysilane molecules. If DFO moieties bind to 100% of the aminopropyl groups on the substrate surface, the calculated maximum coverage of DFO on Celite would be about 5.7 mg/g. However the silica-immobilized DFO product obtained by the procedure described in Example 1 below contains 30 mg DFO/g of product, about six times the calculated amount.

In undertaking the immobilization of a chelator moiety such as DFO on a silica substrate, the reaction of gammaaminopropyltriethoxysilane with high surface area silica in a non-aqueous medium, i.e., toluene, as described in the previously discussed U.S. Pat. Nos. 4,714,556 and 4,787,974, was investigated. For silicas such as Davisil™ 700 (surface area 480 $m^2/g$) and Davisil™ 643 (surface area 300 $m^2/g$), both available from Aldrich Chemical Co., the extent of derivatization of the substrate surface is adequate, but these silicas have high solubility. Similar treatment of silica with lower surface area leads to a material with satisfactory solubility properties. However the number of attachment sites on the substrate surface for binding the chelator moiety is also reduced. Therefore it would be desirable to increase the DFO-binding capacity of such a silica substrate. The process of the present invention makes this possible.

The following examples further illustrate the invention:

Example 1—Immobilization of DFO on a Silica Substrate

A. To a solution of 44 g of 3-aminopropyltriethoxysilane in 2000 ml of deionized (DI) water is added 20.5 g of concentrated hydrochloric acid. The mixture is stirred at room temperature for 30 minutes at pH 2.3. To the resulting solution is added 500 g of Celite Analytical Filter Aid, a diatomaceous earth silica having a surface area of about 5 $m^2/g$, available from Fisher Scientific. The slurry is stirred vigorously for 2 hours; then 900 ml of water is added, and the pH is raised to 10 by the addition of 10% NaOH solution.

B. To a freshly prepared solution of 40 g of DFO in 500 g of DI water is added, with mild agitation, 80 g of 25% glutaraldehyde. Then a dilute solution of sodium tetraborate (0.06 M), prepared by diluting 60 g of 0.2 M borate with 140 g of DI water, is added at a rate of 4 ml/min.

C. The solution prepared in B. is promptly added in portions to the slurry prepared in A. at a rate of 9 ml/min. The reaction is allowed to continue for 15 minutes after completion of the addition. The slurry is filtered through a glass frit funnel into a suction flask containing 6 ml of acetic acid. The solid is washed on the funnel repeatedly with DI water until 7000 ml of filtrate is collected. A sample of the filtrate is analyzed calorimetrically to ascertain the amount of DFO that had not become attached to the substrate. The wet filter cake in the funnel is used in the next step.

D. The wet cake obtained in C. is immediately transferred to a flask to which 3000 ml of DI water is added. The suspension in the flask is stirred until a homogeneous dispersion is obtained; then a freshly prepared solution of 15 g of sodium cyanoborohydride in 100 ml of water is added. The reaction is allowed to proceed, with stirring, for 1 hour. The contents of the flask are then filtered using two glass frit funnels. The flask is rinsed with DI water, and the washings are added to the funnels. The material in the funnels is washed several times with DI water, alternately dispersing the solid by stirring and suctioning off the liquid.

E. The solid obtained in D. is washed with a sequence of liquids in the following order: 1) 1 N acetic acid; 2) 0.9% sodium chloride solution; 3) 1 M urea solution; 4) 1% calcium chloride solution; 5) water; 6) ethanol/water; and 7) ethanol.

For washing with liquids 1)–6), the following procedure is used: half of the solid is placed in each of two glass frit funnels and suspended in 1 liter of the washing fluid. The suspensions are stirred until smooth, then filtered. The collected solids are rinsed twice with water on the funnels, with stirring, the suspensions being filtered after each rinse.

For washing with liquid 7), ethanol, the solids are placed in a single funnel and slurried, with stirring, in 1 liter of 100% ethanol. Following vacuum filtration, the washing is repeated with another 1 liter of 100% ethanol. The solid is collected and dried sufficiently to permit break up to a coarse granular consistency. The product is spread on a tray and allowed to dry at room temperature 48 hours to constant weight.

The dried solid contains 30 milligrams of DFO per gram of chelate-substrate product.

Example 2—Formation of an Extracorporeal Device Containing Immobilized Chelator

The extracorporeal device of the present invention is made using a Fresenius high-flex polysulfone F-60 hollow fiber dialyzer, available from Fresenius AG, Bad Homburg, Germany, which is filled with about 10 grams of the silica-immobilized DFO product obtained as described in Example 1. The filling procedure is similar to that described in Example 7 of the previously mentioned U.S. Pat. No. 4,787,974.

Use of the device of the invention to treat a dialysis patient suffering from ESRD with aluminum overload enables the efficient removal of aluminum from the patient's blood even after a short period of treatment, e.g., 2 hours, with no toxic reactions or other adverse side effects.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed:

1. An extracorporeal device for removing metal cations from blood and other fluids, said device comprising:

a cartridge having an inlet and an outlet and containing a plurality of tubular fibers extending from the inlet to the outlet, each fiber comprising a lumen enclosed by an anisotropic membrane supported by a macroporous structure containing a chelator moiety immobilized on a silica substrate, said membrane forming a diffusion barrier permeable to metal cations contained in the fluid by substantially impermeable to high molecular weight components, wherein said silica substrate comprises particulate silica having a surface area of less than about 50 $m^2/g$.

2. The device of claim 1 wherein said particulate silica has a surface area of less than about 25 $m^2/g$.

3. The device of claim 2 wherein said particulate silica has a surface area of less than about 10 $m^2/g$.

4. The device of claim 1 wherein said chelator moiety is included within a hydroxamic acid compound.

5. The device of claim 4 wherein said hydroxamic acid compound comprises desferrioxamine.

6. The device of claim 1 wherein the chelator moiety immobilized on the silica substrate is the product of reacting gamma-aminopropyltriethoxysilane in an aqueous medium with a substrate comprising particulate silica having a surface of about 5 $m^2/g$ to provide an attachment site on said substrate, covalently binding a connector moiety included within glutaraldehyde to said attachment site, and covalently binding a chelator moiety included within desferrioxamine to said connector moiety.

7. The device of claim 1 wherein said silica substrate comprises diatomaceous earth.

8. A method of removing chelatable metal cations from blood and other fluids, said method comprising:

passing a fluid containing the chelatable metal cations from the inlet to the outlet through the lumen of each tubular fiber included in the extracorporeal device of claim 1;

diffusing the fluid containing said chelatable metal cations through said anisotropic membrane enclosing each said lumen;

contacting said metal cations with said immobilized chelator moieties in the macroporous structure supporting said membrane; and immobilizing said metal cations in said macroporous structure;

whereby said chelatable metal cations are effectively removed from said fluid.

9. The method of claim 8 wherein said substrate comprises diatomaceous earth and said chelator moieties are included within desferrioxamine molecules.

10. The method of claim 8 wherein said chelatable metal cations are selected from the group consisting of aluminum, iron, lead, copper, and mixtures thereof.

11. The method of claim 10 wherein said chelatable metal cations are aluminum.

* * * * *